United States Patent [19]

Fleet et al.

[11] Patent Number: 5,250,703
[45] Date of Patent: Oct. 5, 1993

[54] PYRROLIDIN-3,4-DIOL DERIVATIVES OF HEPTITOLS AND PREPARATION THEREOF

[75] Inventors: George W. J. Fleet, Oxford; Bryan G. Winchester, London, both of United Kingdom

[73] Assignee: Monsanto Company, St. Louis, Mo.

[21] Appl. No.: 954,199

[22] Filed: Sep. 29, 1992

[51] Int. Cl.$^5$ .................. C07D 207/12; C07D 407/06
[52] U.S. Cl. .................... 548/556; 548/110; 534/590
[58] Field of Search ................ 548/556, 110; 534/590

[56] References Cited

U.S. PATENT DOCUMENTS

| | | | |
|---|---|---|---|
| 5,011,929 | 4/1991 | Fleet et al. | 546/14 |
| 5,101,027 | 4/1991 | Fleet et al. | 546/14 |
| 5,136,036 | 3/1992 | Fleet et al. | 546/14 |

OTHER PUBLICATIONS

Choi et al., Tetrahedron Lett. 32, 5517-5520 (1991).
Bruce et al., Tetrahedron 46(1), 19-32 (1990).
Beacham et al., Tetrahedron:Asymmetry 2 (9), 883-900 (1991).
Cenci di Bello et al., Biochem. J. 259, 855-861 (1989).
Carpenter et al., Tetrahedron Lett. 30, 7261 (1989).

Primary Examiner—David B. Springer
Attorney, Agent, or Firm—Scott J. Meyer

[57] ABSTRACT

Novel heptitol analogues of mannofuranose and their syntheses from δ-lactones of heptonic acids are disclosed. The novel heptitols are (A) 2,5-dideoxy-2,5-imino-D-glycero-D-talo-heptitol and (b) 1-amino-2,5-anhydro-1-deoxy-D-glycero-D-talo-heptitol. These novel heptitol compounds are useful inhibitors of glycosidases.

2 Claims, No Drawings

PYRROLIDIN-3,4-DIOL DERIVATIVES OF HEPTITOLS AND PREPARATION THEREOF

BACKGROUND OF THE INVENTION

This invention relates to seven-carbon analogues of mannofuranose and, more particularly, to novel heptitol compounds and their syntheses from δ-lactones of heptonic acids. These novel heptitol compounds are useful inhibitors of glycosidases.

Polyhydroxylated nitrogen heterocycles constitute a major class of glycosidase inhibitors [Winchester and Fleet, *Glycobiology* 2, 199 (1992); G. Legler, *Adv. Carbonhydr. Chem. Biochem.* 48, 319 (1990)] and may also provide clues to the nature of many carbohydrate recognition processes [Furui et al., *Carbohydr. Res.* 229 C1 (1992)]; glycosidase inhibition may be of value in the study of diabetes [Rhinehart et al., *Biochem. Pharmacol.* 39, 1537 (1990); Liu, *J. Org. Chem.* 52 4717 (1987)], cancer [Woynarowska et al., *J., Anticancer Res.* 12, 161 (1992); Liu et al., *Tetrahedrom Lett.* 32, 719 (1991)] and some viral diseases [Jones and Jacob, *Nature* 330, 74 (1991); Taylor et al., *AIDS* 5, 693 (1991); Stephens et al., *J. Virol.* 65, 1114 (1991)]. Because of the potential chemotherapeutic applications of such materials, there is continuing interest in the synthesis of both monocyclic analogues [Lees and Whiteside, *Bioorg. Chem.* 20, 173 (1992); Hassan, *Gazz. Chim. Ital.* 122, 7 (1992); Fairbanks et al., *Tetrahedrom* 48, 3365 (1992)] and bicyclic analogues [Burgess and Henderson, *Tetrahedrom* 48, 4045 (1992); St. Denis and Chan, *J. Org. Chem.* 57, 3078 (1992); Herczegh et al., *Tetrahedron Lett.* 33, 3133 (1992); Gradnig et al., *Tetrahedron Let.* 32, 4489 (1991)]. In particular, the specific inhibition of individual N-linked glycoprotein processing α-mannosidases by nitrogen analogues of mannopyranose [Bischoff and Kornfeld, *Biochem. Biophys. Res. Commun.* 125, 324 (1984); Fuhrmann et al., *Nature* 307, 755 (1984)] and mannofuranose [de Gasperi et al., *J. Biol. Chem.* 267, 9706 (1992) may provide a useful anticancer strategy [White et al., *Cancer, Commun.* 3, 83 (1991); Olden et al., *Pharmacol. Ther.* 50, 285 (1991)].

BRIEF DESCRIPTION OF THE INVENTION

In accordance with the present invention, novel heptitol analogues of mannofuranose and their syntheses from δ-lactones of heptonic acids are provided. These novel heptitol compounds are, respectively, (A) 2,5-dideoxy-2,5-imino-D-glycero-D-talo-heptitol, also designated herein as α-homoDIM (compound 4), and (B) 1-amino-2,5-anhydro-1-deoxy-D-glycero-D-talo-heptitol, also designated herein as α-(aminomethyl)-1-deoxy-mannofuranose (compound 5). These novel heptitol compounds are prepared herein by a novel method of synthesis from the acetonides of glycero-talo- and glycero-galacto-heptono-lactone.

The starting δ-lactones of heptonic acids are 3,4:6,7-di-O-isopropylidene-D-glycero-D-galacto-heptono-1,5-lactone (compound 7) and 3,4:6,7-di-O-isopropylidene-D-glycero-D-talo-heptono-1,5-lactone (compound 10). These starting compounds are known materials described by Bruce et al., *Tetrahedron* 46(1), 19–32 (1990); Beacham et al., *Tetrahedron Asymmetry* 2(9), 883–990 (1991); and by Fleet and Bruce, U.S. Pat. Nos. 5,011,929, 5,101,027, and 5,136,036. They are also conveniently prepared from diacetone mannose (compound 6).

The novel heptitol compounds of this invention are useful inhibitors of glycosidases. Their activity is demonstrated herein against eleven different types of human liver glycosidases by a conventional enzyme assay method described by Cenci di Bello et al., *Biochem. J.* 259, 855–861 (1989). Although the novel α-homoDIM (4) can be considered structurally as a derivative of the known α-mannosidase inhibitor, deoxymannojirimycin (DMJ, compound 1), in which an anomeric α-hydroxymethyl group has been added to a polyhydroxylated pyrrolidine ring, it unexpectedly is about twice as effective as DMJ in its inhibitory activity against α-mannosidase but much less potent in its inhibitory activity against α-fucosidase. On the other hand, the novel α-(aminomethyl)-1-deoxy-mannofuranose (5) unexpectedly is a moderate inhibitor of α-fucosidase but relatively inactive against α-mannosidases. As such, the novel heptitol compounds of this invention are also useful in enzyme assays employing α-mannosidase or α-fucosidase enzyme catalyzed reactions.

DETAILED DESCRIPTION OF THE INVENTION

The invention is conveniently illustrated by the following description of preferred embodiments in which compounds are shown both by chemical structure and by compound numbers in parentheses. Reference cited in the detailed description of the invention are listed at the end.

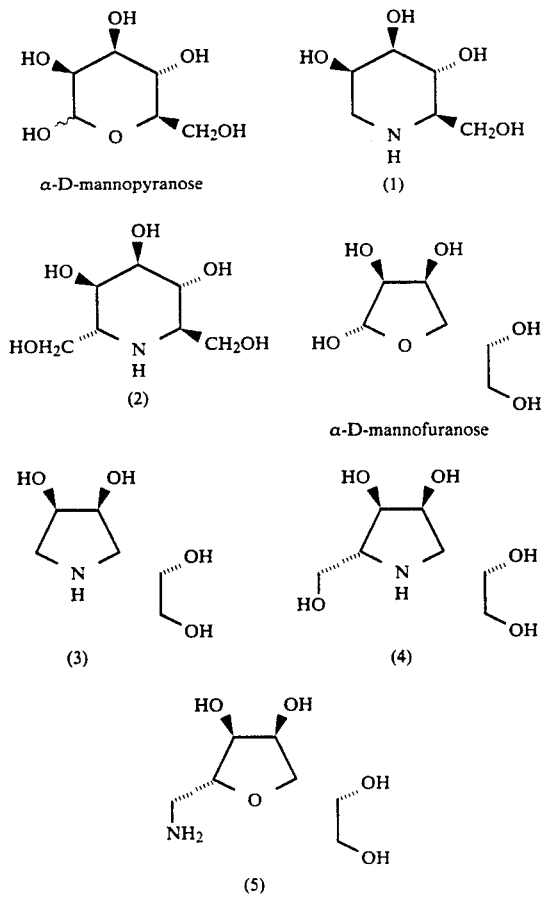

Syntheses of α-homoDIM (4) and α-(aminomethyl)-1-deoxy-mannofuranose (2)

Both materials were synthesized from the seven-carbon epimeric alcohols (7) and (10), both of which are obtained from the Kiliani ascension[13] of diacetone mannose (6) [Scheme 1]. The tetrahydrofuran ring in (5) is formed by displacement of a leaving group from C-2 of the sugar by the lactone ring oxygen with inversion of configuration at C-2 and retention of configuration at C-5. The pyrrolidine ring in (4) is formed by introduction of nitrogen with retention of configuration at C-2 of the alcohol (10) [the major product of the Kiliani reaction], followed by joining the nitrogen function at C-2 to C-5 with overall retention of configuration, achieved by a double inversion of configuration at C-5; a somewhat analogous strategy has been used for the construction of the pyrrolidine ring in the syntheses of DIM (3)[12] and of diastereomers of the bicyclic alkaloid, alexine.[14]

epimeric at C-2 of the lactone. The key step in the synthesis is a ring contraction reaction of the mesylate (8) induced by methoxide, in which the leaving group at C-2 is displaced by the ring oxygen function; addition of solid potassium carbonate to a methanolic solution of the mesylate (8) resulted in an efficient ring contraction to the tetrahydrofuran ester (12) [81% yield]. This transformation proceeds by nucleophilic addition of methoxide to the lactone carbonyl, ring opening and subsequent ring closure by nucleophilic displacement of the mesylate by the C-5 oxygen function; the overall stereochemical result of this sequence is inversion of configuration at C-2 of the sugar. The iodide (9) may be prepared from the major product (10) of the Kiliani ascension; conversion of the alcohol (10) to the corresponding triflate followed by treatment with tetrabutyl ammonium iodide give the iodide (9) in quantitative yield. This iodide (9) on treatment with potassium carbonate in methanol underwent a similarly efficient ring contraction to give the methyl ester (12) in 80% yield.

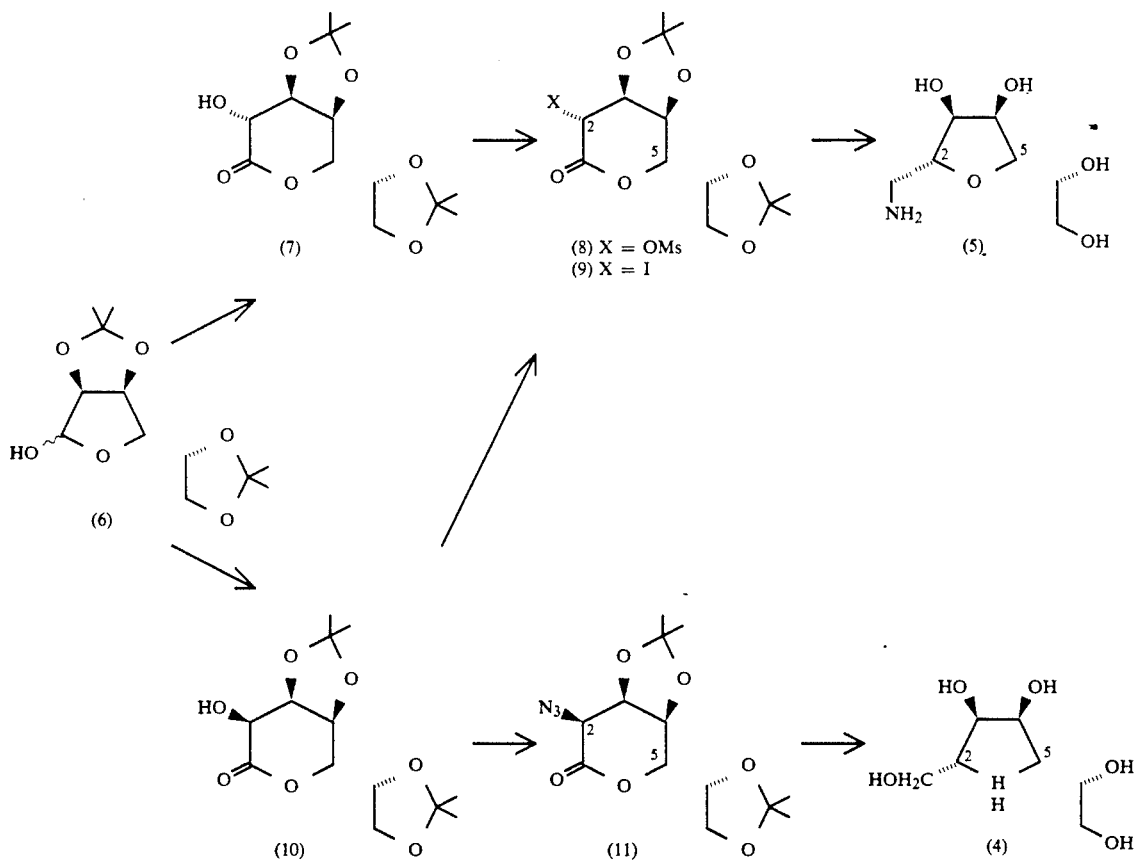

Scheme 1

For the syntheses of the tetrahydrofuran analogue (5) [Scheme 2], the galacto-alcohol (7) was treated with mesyl chloride in pyridine to give the mesylate (8) [83% yield], together with a small amount of the mesylate This general reaction of δ-lactones with α-leaving groups provides a powerful strategy for the synthesis of tetrahydrofurans with carbon substituents at C-2 and C-5[15].

Scheme 2

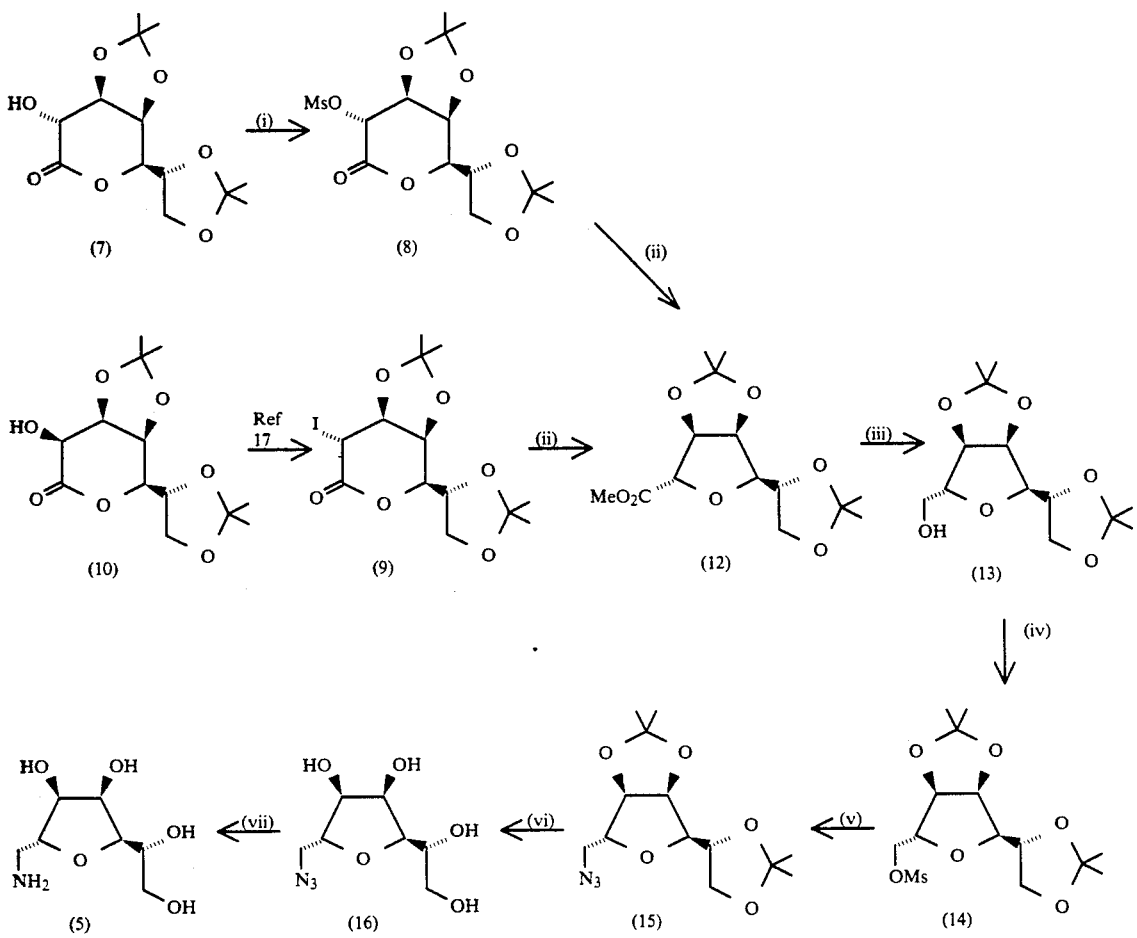

(i) MsCl, pyridine, room temp. 3 h
(ii) K₂CO₃, MeOH, room temp. 3 h
(iii) LiAlH₄, Et₂O
(iv) MsCl, py, CH₂Cl₂, 0° C.
(v) NaN₃, DMF, 40° C., 24 h;
(vi) TFA, H₂O, room temp. 2 h
(vii) H₂, MeOH, 10% Pd/C, room temp. 24 h; then HCl (aq).

Subsequent functional group manipulations on (12) gave the furan analogue (5). The ester (12) was reduced by lithium aluminum hydride in ether to the primary alcohol (13) [83% yield] which was esterified by mesyl chloride in pyridine to afford the mesylate (14) [95% yield]. Nucleophilic displacement of the mesylate function in (14) by sodium azide in dimethylformamide gave the corresponding azide (15) [51% yield] from which the isopropylidene protecting groups were removed by treatment with aqueous trifluoroacetic acid to give the azidotetraol (16) [75% yield]. Subsequent hydrogenation of the azide (16) in methanol in the presence of palladium gave the required aminomethyl furanose analogue (5), isolated as the crystalline hydrochloride [88% yield–18% overall yield for either the six steps from (7) or the seven steps from (10)].

For the synthesis of α-homoDIM (4) [Scheme 3], the alcohol (10) was converted, with overall retention at C-2, to the azide (11) as previously described.[16] Attempts at the direct reduction of the azidolactone (11) to the azidodiol (18) were unsuccessful; accordingly the lactone (11) was reduced first by diisobutylaluminum hydride to the lactol (17) which, on subsequent treatment with sodium borohydride, gave the required diol (18) [78% overall yield]. The primary hydroxyl group was protected as the diphenyl-tert-butylsilyl ether (19) [92% yield] which on treatment with mesyl chloride in pyridine gave the azidomesylate (20) [90%]. Selective hydrolysis of the terminal acetonide in (20) with aqueous acetic acid gave the monoacetonide (21) [79% yield] together with a small amount of the completely deprotected tetraol [4% yield]. Treatment of the dihydroxymesylate (21) with barium methoxide gave the epoxide (22) [84% yield]. Hydrogenation of (22) gave relatively complex mixtures; accordingly, the primary hydroxyl group in (22) was protected as the tert-butyldimethylsilyl ether (23) [84% yield] which on hydrogenation in ethanol in the presence of palladium black gave the protected pyrrolidine (24) in 75% yield. Removal of both silyl protecting groups and also of the isopropylidene group from (24) was achieved by aqueous trifluoroacetic acid to give α-homoDIM (4) [78% yield] as the crystalline hydrochloride salt [21% overall yield from the azidolactone (11)].

Scheme 3

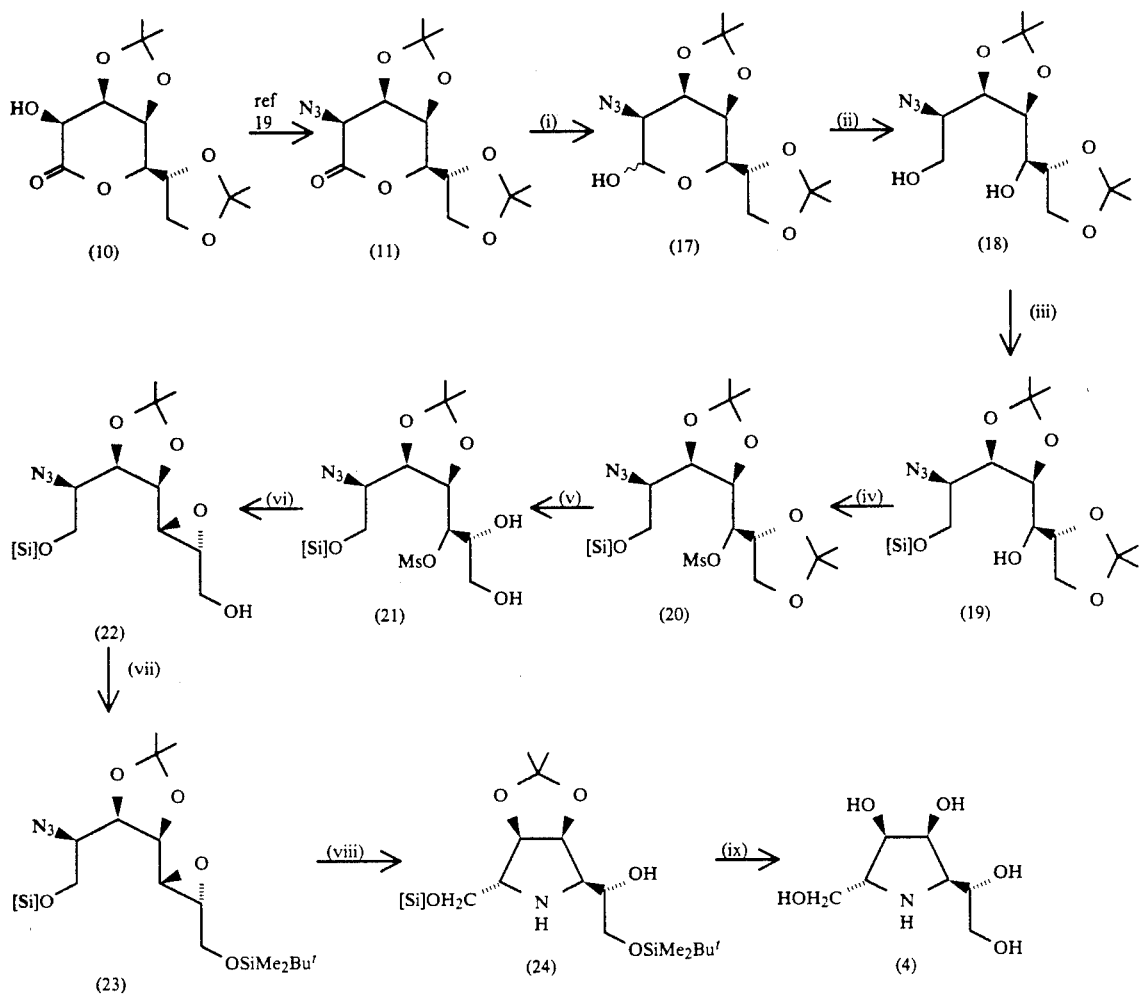

(i) iso-Bu₂AlH in THF
(ii) NaBH₄ in MeOH
(iii) Ph₂Bu'SiCl, imidazole, DMF, 0° C.,
(iv) MsCl, DMAP in pyridine
(v) MeCOOH in aq. 1,4-dioxan
(vi) Ba(OMe)₂ in MeOH, 0° C.
(vii) Me₂Bu'SiCl, imidazole, DMF, 0° C.
(viii) H₂, Pd black, EtOH
(ix) CF₃COOH/H₂O, 48 h Glycosidase Inhibition Human liver glycosidases were assayed in the absence and presence [1 mM] of each of the potential inhibitors, using the appropriate buffered 4-methylumbelliferyl glycosides as substrates, as previously described.[17] See Table I, below. The seven-carbon compounds (2) and (4) can be considered as derivatives of the mannopyranose analogue, DMJ (1), and the mannofuranose analogue, DIM (3), in which an anomeric α-hydroxymethyl group has been introduced into the unsubstituted carbon atom of the ring. The addition of the anomeric substituent to DMJ does not affect appreciably the inhibition of the multiple forms of α-mannosidase, but it does abolish the moderate inhibition of β-hexosaminidase and decrease markedly the potent inhibition of α-fucosidase (Table). α-HomoDMJ (2) is thus a much more selective inhibitor of α-mannosidases than is the parent compound DMJ (1). The loss of inhibition of β-hexosaminidase can probably be attributed to the hydrophilic nature and incorrect configuration of the hydroxymethyl substituent; in general, analogues with hydrophobic groups on the anomeric carbon or the ring nitrogen bind more strongly to hexosaminidase. The decrease in inhibition of α-fucosidase can be understood by comparing the structure of α-homoDMJ with other derivatives of DMJ that inhibit α-fucosidase.[18] Both DMJ (1) and α-homoDMJ possess the minimum structural requirement for the inhibition of α-fucosidases by polyhydroxylated piperidines, that is the correct absolute configuration of the three secondary hydroxyl groups is the same for both D-mannose and L-fucose.

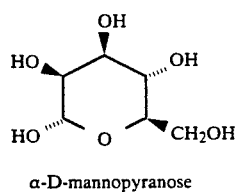
α-D-mannopyranose
-continued
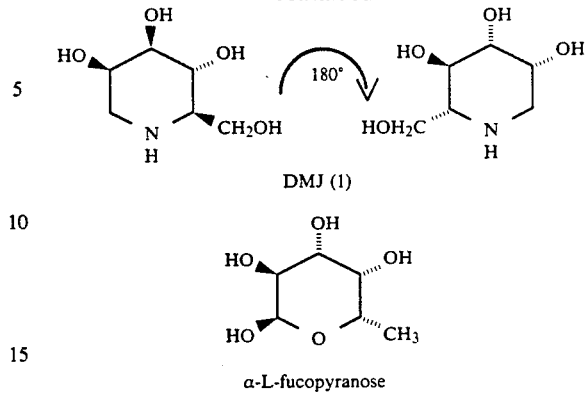
DMJ (1)
α-L-fucopyranose

TABLE 1

% Inhibition of Glycosidase Activity at 1 mM concentration of inhibitor

| Enzyme | DMJ (1) | αHomoDMJ (2) | DIM (3) | α-HomoDIM (4) | Manhepamine (5) |
|---|---|---|---|---|---|
| α-Mannosidase | | | | | |
| Lysosomal | 58 | 49 | 97 $K_i$ 13 μM | 71 | 2 |
| Neutral | 30 | 33 | 89 | 76 | 2 |
| Golgi | 45 | 56 | 96 | 92 | not determined |
| β-Mannosidase | 0 | 0 | 0 | 18 | 3 |
| α-Glucosidase | 21 | 4 | 0 | 12 | 0 |
| β-Glucosidase | 0 | 0 | 16 | 23 | 14 |
| α-Galactosidase | 0 | 0 | 0 | 11 | 0 |
| β-Galactosidase | 0 | 0 | 76 | 35 | 0 |
| β-Hexosaminidase | 55 | 1 | 28 | 0 | 46 |
| α-Fucosidase | 92 $K_i$ 5 μM | 29 | 24 | 27 | 77 |
| β-Glucuronidase | 53 | 0 | 9 | 0 | 7 |
| α-Arabinosidase | 5 | 0 | 66 | 25 | 0 |
| β-Xylosidase | 3 | 0 | 45 | 21 | 6 |

Although α-L-fucosidase is inhibited strongly by some compounds which have either a different substituent to the methyl group of fucose or a substituent with the incorrect configuration at the anomeric position, incorrect substituents at both positions lead to a significant loss of inhibition even though the configuration of the secondary hydroxyl groups is correct.

The mannofuranose analogue DIM (3) is a much more potent inhibitor than the piperidine analogues (1) and (2) of all the mannosidases investigated. The introduction of the anomeric hydroxymethyl group to give α-HomoDIM (4) decreases the inhibition of the lysosomal and neutral enzymes, but not of the Golgi α-mannosidase. These results confirm that the binding of aminosugars to α-mannosidases does not require an anomeric substituent; the introduction of the substituent changes the relative specificity of the inhibitor while still retaining significant inhibitory properties towards α-mannosidases. thus the homologues (2) and (4) may allow the further development of substituents in the anomeric position which are specific inhibitors for individual processing α-mannosidases. None of nitrogen heterocycles (1)–(5) inhibit β-mannosidase, suggesting this enzyme has a strict requirement for a β-anomeric substituent in order to bind strongly.

The tetrahydrofuran derivative (5), which is related to α-HomoDIM (4) by interchanging the ring nitrogen and the exocyclic oxygen, did not inhibit any of the α-mannosidases, indicating the need of the ring nitrogen to be protonated rather than an exocyclic amine. The structural basis for the moderate inhibition of α-fucosidase by (5) is unobvious and is interesting in view of the recent report[19] of the inhibition of a mammalian α-fucosidase by the furanose analogue of deoxyfuconojirimycin. The amino group on the anomeric substituent of (5) is probably responsible for the weak inhibitory properties towards β-N-acetylhexosaminidase.

In a preferred embodiment of the synthesis of α-(aminomethyl)-1-deoxy-mannofuranose (5) from the galacto-lactone (7), the following reaction steps are carried out:

a. reacting 3,4:6,7-di-O-isopropylidene-D-glycero-D-galacto-heptono-lactone (7) with mesyl chloride to give the corresponding mesylate (8), b. reacting the mesylate (8) with potassium carbonate to produce ring contraction to the tetrahydrofuran ester (12) with inversion of configuration at C-2, c. reducing the tetrahydrofuran ester (12) with lithium aluminum hydride to give the primary alcohol (13), d. esterifying the primary alcohol (13) at C-1 with mesyl chloride to afford the mesylate (14), e. displacing the mesylate function in mesylate (14) with alkali metal azide, e.g., sodium azide, to give the corresponding azide (15), f. removing the isopropylidene protecting groups from azide (15) by acid hydrolysis, e.g., with trifluoroacetic acid, to give the corresponding azidotetraol (16), and g. subjecting the azidotetraol (16) to palladium catalyzed reductive hydrogenation to form the desired α-(aminomethyl)-1-deoxy-mannofuranose.

Alternatively, the tetrahydrofuran ester (12) used in the foregoing synthesis can be prepared from the talo-lactone (10) by the following reaction steps:

a. reacting 3,4:6,7-di-O-isopropylidene-D-glycero-D-galacto-heptono-lactone (10) with trifluoromethanesulfonic anhydride to give the corresponding triflate followed by treating with iodide salt, e.g., tetrabutyl ammonium iodide, to give the iodide (9), b. reacting the iodide (9) with potassium carbonate to produce ring contraction to the tetrahydrofuran ester (12) with inversion of configuration at C-2.

In a preferred embodiment of the synthesis of α-homoDIM (4), the talo-lactone (10) is esterified with triflic anhydride followed by treatment with alkali metal azide, e.g., sodium azide, to give the azidolactone (11) as described by Bruce et al., *Tetrahedron* 46, 19–32 (1990) and by Fleet and Bruce, U.S. Pat. No. 5,011,929. The following reaction steps are then carried out for the synthesis of α-homoDIM from the previously known azidolactone (11):

a. reducing 2-azido-2-deoxy-3,4:6,7-di-O-isopropylidene-D-glycero-D-talo-heptono-1,5-lactone (11) by di-isobutylaluminum hydride to the corresponding lactol (17), b. reacting the lactol (17) with alkali metal borohydride, e.g., sodium borohydride, to provide ring opening and give the diol (18), c. reacting the diol (18) with tert-butyldiphenylsilylchloride to protect the primary hydroxyl group as the tert-butyldiphenylsilyl ether (19), d. esterifying the hydroxyl of the tert-butyldiphenylsilyl ether at C-5 with mesyl chloride to give the azidomesylate (20), e. selectively hydrolyzing the terminal acetonide in the azidomesylate (20) with organic acid, e.g., acetic acid, to give the monoacetonide (21), f. treating the monoacetonide (21) with barium methoxide to give the epoxide (22), g. reacting the epoxide (22) with tert-butyldimethylsilylchloride to protect the primary hydroxyl group as the tert-butyldimethylsilyl ether (23), h. hydrogenating the tert-butyldimethylsilyl ether (23) in the presence of palladium black to give the protected pyrrolidine (24), i. removing all the hydroxyl protecting groups in the protected pyrrolidine (24) by acid hydrolysis, e.g., with trifluoroacetic acid, to give the desired α-homoDIM.

Other such suitable reactants for use in the foregoing syntheses of the α-(aminomethyl)-1-deoxy-mannofuranose and the α-homoDIM will be apparent to the person skilled in the art after reading the present disclosure. These reactants are generally used in proportions such as to satisfy the stoichiometry of the above reaction steps and shown in the above reaction schemes 1, 2 and 3. Illustrative of such suitable reactants are the use of sodium azide, potassium azide, lithium azide and tetrabutylammonium azide to introduce the azide function; use of hydroxyl protecting groups formed from ketones, dialkylketones and cycloalkylketones to provide groups such as isopropylidene and cyclohexylidene; use of sodium borohydride, potassium borohydride and borane-dimethyl sulfide as reducing agents; use of noble metal catalysts such as Pd and Pt on carbon for catalytic hydrogenation; use of electrophiles such as triflic anhydride, tosyl chloride, benzyl sulfonyl chloride and mesyl chloride for the esterification of hydroxyls; and use of organic solvents such as dioxane, DMF, DMSO, THF, N-methylpyrrolidine, pyridine, acetonitrile and the like as solvent media for the reaction steps. The use of these and other such reactants in the syntheses of the present invention will be apparent to the person skilled in the art after reading the disclosure herein.

The following examples will further illustrate the invention in greater detail although it will be appreciated that the invention is not limited to these specific examples or the detailed process conditions recited therein which are provided by way of exemplification and not limitation.

EXAMPLES

General Procedures

Melting points were recorded on a Kofler hot block and are uncorrected. Proton nuclear magnetic resonance ($\delta_H$) spectra were recorded on Varian Gemini 200 (200 MHz) or Bruker WH 300 (300 MHz) spectrometers. $^{13}$C Nuclear magnetic resonance ($\delta_C$) spectra were recorded on a Varian Gemini 200 (50 MHz) spectrometer and multiplicities were assigned using DEPT sequence. $^{13}$C spectra run in $D_2O$ were referenced to methanol ($\delta_C$ 49.6 ppm) as an internal standard. All chemical shifts are quoted on the $\delta$-scale. Infra-red spectra were recorded on a Perkin-Elmer 781 or on a Perkin-Elmer 1750 FT spectrophotometer. Mass spectra were recorded on VG Micromass ZAB 1F, Masslab 20–250 or Trio-1 GCMS (CG-5 column) spectrometers using desorption chemical ionisation ($NH_3$, DCI) or chemical ionisation ($NH_3$, CI), as stated. Optical rotations were measured on a Perkin-Elmer 241 polarimeter with a path length of 1 dm. Concentrations are given in g/100 ml. Microanalyses were performed by the microanalysis service of the Dyson-Perrins Laboratory. Thin layer chromatography (t.l.c.) was carried out on aluminium sheets coated with 60F$_{254}$ silica or glass plates coated with silica Blend 41. Plates were developed using a spray of 0.2% w/v cerium (IV) sulphate and 5% ammonium molybdate in 2M sulphuric acid or 0.5% ninhydrin in methanol (for amines). Flash chromatography was carried out using Sorbsil C60 40/60 silica. Ion exchange columns were packed with 'Dowex' 50W-X8 resin in the H+ form. Solvents and commercially available reagents were dried and purified before use according to standard procedures; dichloromethane was refluxed over and distilled from calcium hydride, methanol was distilled from magnesium methoxide, pyridine was distilled from, and stored over, potassium hydroxide; tetrahydrofuran was distilled, under nitrogen, from a solution dried with sodium in the presence of benzophenone. Hexane was distilled at 68° C. before use to remove involatile fractions. The epidermic alcohols (7) and (10) were obtained from diacetone mannose;[14] the azide (11)[19] and iodide (9)[17] were prepared from (10). Deoxymannojirimycin (1)[12] and DIM (3)[13] were synthesised as previously described.

Synthesis of α-(aminomethyl)-1-deoxy-mannofuranose (5)

Example 1

3,4:6,7-Di-O-isopropylidene-2-O-methanesulphonyl-D-glycero-D-galacto-heptono-1,5-lactone (8). Methane-sulphonyl chloride (2.6 ml, 26 mmol) was added dropwise over 2 min to a stirred solution of the galactolactone (7) (3.0 g, 10 mmol) in dry pyridine (5 ml) at 0° C. under nitrogen. After a further 3 h, $^1$H NMR of the crude reaction mixture indicated that no starting material remained. The solvent was removed in vacuo , and the residue dissolved in chloroform (50 ml), washed with dilute hydrochloric acid (3×30 ml), water (2×30 ml), brine (2×20 ml) and dried (magnesium sulphate). The solvent was removed in vacuo and the residue purified by flash chromatography (ether:hexane, 1:1) to give 3,4:6,7-di-O-isopropylidene-2-O-methanesulphonyl-D-glycero-D-galacto-heptono-1,5-lactone (8) (2.49 g, 83%) m.p. 136°–137° C. (Found: C, 45.72; H, 6.16. $C_{14}H_{22}O_9S$ requires C, 45.89; H, 6.05%); $[\alpha]_{D20}+67.4°$ (c 1.0 in $CHCl_3$);$\delta_H(CDCl_3)$ 1.40, 1.44, 1.48 (12H, 3×s, 4×Me), 3.15 (3H, s, —SO$_2$Me), 4.11 (1H, dd, H-7, $J_{6,7}$ 3.9 Hz, $J_{7,7'}$ 9.3 Hz), 4.17 (1H, dd, H-7', $J_{6,7'}$ 5.6 Hz), 4.41 (1H, ddd, H-6, $J_{5,6}$ 8.3 Hz), 4.48 (1Y, dd, H-5, $J_{4,5}$ 1.5 Hz), 4.70 (1H, dd, H-4, $J_{3,4}$ 7.4 Hz), 4.78 (1H, dd, H-3, $J_{2,3}$ 2.3 Hz), 5.02 (1H, d, H-2); $\delta_C(CDCl_3)$ 23.9, 24.8, 25.6, 26.8 (4×q, 4×Me), 38.6 (q, —SO$_2$Me), 66.4 (t, C-7), 70.5, 72.7, 73.4, 74.2, 76.8 (5×d, C-2, C-3, C-4, C-5, C-6), 110.1, 111.2 (2×s, 2×CMe$_2$), 163.6 (s, C-1); m/z ($NH_3$, DCI) 384 (M+$NH_{4+}$, 100%), 367 (M+H+, 80%). A small amount of the mesylate epimeric at C-2 (0.19 g, 5%) was also formed.

Example 2

Methyl 2,5-anhydro-3,4:6,7-di-O-isopropylidene-D-glycero-D-talo-heptaonat (12) (i) From mesylate (8): Potassium carbonate (1.10 g, 7.93 mmol) was added to a solution of the mesylate (8) (2.90 g, 7.93 mmol) in dry methanol (25 ml) and the reaction mixture stirred at room temperature. After 4 h, t.l.c. (hexane:ethyl acetate, 1:1) indicated complete conversion of the starting material ($R_f$ 0.7) to a single product ($R_f$ 0.8). The solution was filtered and the solvent removed in vacuo. The residue was purified by flash chromatography (hexane:ethyl acetate, 4:1) to give methyl 2,5-anhydro-3,4:6,7-di-O-isopropylidene-D-glycero-D-talo-heptonate (12) (1.94 g, 81%) m.p. 79°–80° C. (Found: C, 55.91; H, 8/45. $C_{14}H_{22}O_7S$ requires C, 55.64; H, 7.34%); $[\alpha]_{D20}-11.4°$ (c 1.0 in $CHCl_3$); $\delta_H$ ($CDCl_3$) 1.36, 1.39, 1.46, 1.52 (12H, 4×s, 4×Me), 3.77 (3H, s, —CO$_2$Me), 4.01 (1H, dd, H-5, $J_{4,5}$ 3.7 Hz, $J_{5,6}$ 7.9 Hz), 4.11 (1H, dd, H-7, $J_{6,7}$ 5.6 Hz), 4.14 (1H, dd, H-7', $J_{6,7'}$ 5.8 Hz), 4.41 (1H, dt, H-6), 4.56 (1H, br s, H-2), 4.81 (1H, dd, H-4, $J_{3,4}$ 6.0 Hz), 4.97 (1H, dd, H-3, $J_{2,3}$ 0.7 Hz); $\delta_C$ ($CDCl_3$) 24.5, 24.9, 25.8, 26.6 (4×q, 4×Me), 52.1 (q, —CO$_2$Me), 66.9 (t, C-7), 72.9, 80.4, 82.8, 84.1 (5×d, C-2, C-3, C-4, C-5, C-6) 109.3, 113.3 (2×s, 2×Cme$_2$), 1.70.7 (s, C-1); m/z ($NH_3$, CI) 320 (M+$NH_{4+}$, 10%), 303 (M+H+, 100%).

(ii) from iodide (9): Potassium carbonate (56 mg, 0.40 mmol) was stirred with a solution of the iodide (9) (0.16 g, 0.40 mmol) in methanol (20 ml) at room temperature. After 4 h, t.l.c. (hexane:ethyl acetate, 1:1) indicated complete conversion of the starting material ($R_f$ 0.8) to a single product ($R_f$ 0.7). The solution was filtered and the solvent removed in vacuo. The residue was purified by flash chromatography (hexane:ethyl acetate, 4:1) to give methyl 2,5-anhydro-3,4:6,7-di-O-isopropylidene-D-glycero-D-talo-heptonate (12) as a colourless crystalline solid (97 mg, 80%), m.p. 79°–80° C., identical by $^1$H NMR to that obtained above from the mesylate (8).

Example 3

2,5-Anhydro-3,5:6,7-di-O-isopropylidene-D-glycero-D-talo-heptitol (13). Lithium aluminium hydride (95.0 mg, 2.49 mmol) was added in small portions to a solution of the ester (12) (0.50 g, 1.66 mmol) in dry ether (5 ml) and the reaction mixture stirred at 0° C. under nitrogen. After 20 min, t.l.c. (hexane:ethyl acetate, 1:1) indicated complete conversion of the starting material ($R_f$ 0.8) to a single product ($R_f$ 0.3). The reaction was quenched by the addition of sodium fluoride (0.10 g, 1.66 mmol) and a few drops of water. The reaction mixture was filtered, the solvent removed in vacuo, and the residue purified by flash chromatography (hexane:ethyl acetate, 3:1) to give 2,5-anhydro-3,4:6,7-di-O-isopropylidene-D-glycero-D-talo-heptitol (13) (0.38 g, 83%) a colourless crystalline solid, m.p. 82°–83° C. (Found: C, 57.02; H, 8.37. $C_{13}H_{22}O_6$ requires C, 56.92; H, 8.08%); $[\alpha]_{D20}$ −6.9° (c 1.0 in $CHCl_3$); $\delta_H$ ($CDCl_3$) 1.36, 1.39, 1.46, 1.52 (12H, 4×s, 4×Me), 1.83 (1H, br s, OH), 3.63 (2H, br d, H-1, H-1′, J 5.0 Hz), 3.99 (1H, dd, H-5, $J_{4,5}$ 3.9 Hz, $J_{5,6}$ 7.1 Hz), 4.07 (1H, dd, H-7, $H_{6,7}$ 5.0 Hz, $J_{7,7'}$ 8.8 Hz), 4.11 (1H, dd, H-7′, $J_{6,7'}$ 6.3 Hz), 4.17 (1H, br t, H-2), 4.40 (1H, m, H-6), 4.68 (1H, dd, H-3, $J_{2,3}$ 1.3 Hz, $J_{3,4}$ 6.1 Hz), 4.81 (1H, dd, H-4); $\delta_C$ ($CDCl_3$) 24.4, 24.9, 25.9, 26,6 (4×q, 4×Me), 62.0, 66.4 (2×t, C-1, C-7), 73.7, 81.0, 81.3, 82.5, 84.8 (5×d, C-2, C-3, C-4, C-5, C-6), 109.0, 112.8 (2×s, 2×$Cme_2$); m/z ($NH_3$, CI) 292 ($M+NH_{4+}$, 5%), 275 ($M+H^+$, 80%), 217 (100%).

Example 4

2,5-Anhydro-3,4:6,7-di-O-isopropylidene-D-glycero-D-talo-heptitol (14). Methanesulphonyl chloride (1.18 ml, 11.8 mmol) was added dropwise over 2 min to a stirred solution of the taloheptitol (13) (1.40 g, 4.0 mmol) in dry pyridine (5 ml) and dichloromethane (5 ml) at 0° C. under nitrogen. After a further 30 min, t.l.c. (hexane:ethyl acetate, 1:1) indicated complete conversion of the starting material ($R_f$ 0.3) to a single product ($R_f$ 0.6). The solvent was removed in vacuo, the residue dissolved in chloroform (50 ml), washed with dilute hydrochloric acid (3×30 ml), water (2×30 ml), brine (2×20 ml) and dried (magnesium sulphate). The solvent was removed in vacuo and the residue purified by flash chromatography (ether:hexane 1,:1) to give 2,5-anhydro-3,4:6,7-di-O-isopropylidene-1O-methanesulphonyl-D-glycero-D-talo-heptitol (14) (1.70 g, 95%), a colourless crystalline solid, m.p. 102° C. (Found: C, 47.89; H, 7.04. $C_{14}H_{24}O_8S$ requires C, 47.72; H, 6.87%); $[\alpha]_{D20}$ −5.9° (c 1.0 in $CHCl_3$); $\delta_H$($CDCl_3$) 1.33, 1.39, 1.45, 1.48 (12H, 4×s, 4×Me), 3.06 (3H, s, —$SO_2Me$), 3.59 (1H, dd, H-5, $J_{4,5}$ 3.3 Hz, $J_{5,6}$ 7.3 Hz), 3.88 (1H, m, H-2), 4.04 (1H, dd, H-7, $J_{6,7}$ 4.7 Hz, $J_{7,7'}$ 8.7 Hz), 4.10 (1H, dd, H-7′, $J_{6,7'}$ 6.0 Hz), 4.40 (1H, dd, H-1, $J_{1,1'}$ 11.2 Hz, $J_{1,2}$ 7.1 Hz), 4.41 (1H, m, H-6), 4.50 (1H, dd, H-1′, $J_{1',2}$ 4.5 Hz), 4.76 (1H, dd, H-3, $J_{2,3}$ 3.5 Hz, $J_{3,4}$ 6.1 Hz), 4.80 (1H, dd, H-4); $\delta_C$($CDCl_3$) 24.2, 25.0, 25.5, 26.7 (4×q, 4×Me), 37.3 (q, —$SO_2Me$), 66.6, 67.8 (2×t, C-1, C-7), 72.8, 79.0, 80.4, 80.5, 82.0 (5×d, C-2, C-3, C-4, C-5, C-6), 109.2, 113.1 (2×s, 2×$CMe_2$); m/z ($NH_3$, DCI) 370 ($M+NH_{4+}$, 15%), 353 ($M+H^+$, 100%).

Example 5

2,5-Anhydro-3,4:6,7-di-O-isopropylidene-D-glycero-D-talo-heptitol (15). Sodium azide (0.98 g, 15 mmol) was added to a solution of the mesylate (14) (1.70 g, 4.8 mmol) in dry DMF (10 ml) and the reaction mixture stirred at 40° C. After 24 h, t.l.c. (ethyl acetate:hexane, 3:1) indicated partial conversion of the starting material into a single product. The solvent was removed in vacuo and the residue dissolved in dichloromethane, washed with water (3×20 ml) and dried over magnesium sulphate. The product was separated from the remaining starting material by flash chromatography (ether:hexane, 1:1) to give 2,5-anhydro-3,4:6,7-di-O-isopropylidene-D-glycero-D-talo-heptitol (15), (0.66 g, 44%, 51% based on recovered starting material), a colourless crystalline solid, m.p. 69° C. (Found: C, 52.35; H, 7.35; N, 13.97. $C_{13}H_{21}O_5N_3$ requires C, 52.17; H, 7.07; N, 14.07%); $[\alpha]_{D20}$ −7.1° (c 1.0 in $CHCl_3$); $\nu_{max}$ (KBr disc) 2093 ($N_3$) $cm^{-1}$; $\delta_H$($CDCl_3$) 1.36, 1.39, 1.46, 1.52 (12H, 4×s, 4×Me), 3.25 (1H, dd, H-1, $J_{1,1'}$ 12.9 Hz, $J_{1,2}$ 4.7 Hz ), 3.45 (1H, dd, H-1′, $J_{1',2}$ 6.6 Hz), 3.95 (1H, dd, H-5, $J_{4,5}$ 3.8 Hz, $J_{5,6}$ 7.5 Hz), 4.06 (1H, dd, H-7, $J_{6,7}$ 4.7 Hz, $J_{7,7'}$ 8.8 Hz), 4.11 (1H, dd, H-7′, $J_{6,7'}$ 6.0 Hz), 4.24 (1H, br t, H-2), 4.40 (1H, ddd, H-6), 4.65 (1H, dd, H-3, $J_{2,3}$ 1.3 Hz, $J_{3,4}$ 6.1 Hz), 4.82 (1H, dd, H-4); $\delta_C$ ($CDCl_3$) 24.5, 24.9, 26.0, 26.7 (4×q, 4×Me), 51.3, 66.7 (2×t, C-1, C-7), 73.3, 81.0, 81.6, 83.2, 83.6 (5×d, C-2, C-3, C-4, C-5, C-6), 109.3, 113.1 (2×s, 2×$CMe_2$); m/z ($NH_3$, DCI) 317 (M30 $NH_{4+}$, 5%), 300 ($M+H^+$, 100%).

Example 6

2,5-anhydro-3,4:6,7-di-O-isopropylidene-D-glycero-D-talo-heptitol (16). The azide (15) (0.52 g, 1.72 mmol) was stirred in trifluoroacetic acid:water, 1:1 (5 ml) at room temperature. After 2 h, t.l.c. (5% methanol in ethyl acetate) indicated complete conversion of the starting material ($R_f$ 1.0) to a single product ($R_f$ 0.3). The solvent was removed in vacuo, and the co-evaporated with toluene (3×10 ml) to remove the last traces of acid. The residue was taken up in methanol and preabsorbed on to silica before purification by flash chromatography (1% methanol in ethyl acetate) to give 2,5-anhydro-3,4:6,7-di-O-isopropylidene-D-glycero-D-talo-heptitol (16) (0.28 g, 75%), m.p. 86° C. (Found: C, 38.18; H, 6.09; N, 18.89. $C_7H_{13}O_5N_3$ requires C, 38.36; H, 5.98; N, 19.17%) $[\alpha]_{D20}$ +71.5° (c 1.0 in $CHCl_3$); $\nu_{max}$(KBr disc) 2108 ($N_3$) $cm^{-1}$; $\delta_H$($CD_3OD$) 3.25 (1H, dd, H-1, $J_{1,1'}$ 13.2 Hz, $J_{1,2}$ 5.2 Hz), 3.51 (1H, dd, H-1′, $J_{1',2}$ 2.7 Hz), 3.55 (1H, dd, H-7, $J_{6,7}$ 6.0 Hz, $J_{7,7}$ 11.5 Hz), 3.77 (1H, dd, H-7′, $J_{6,7'}$ 3.0 Hz), 3.86 (1H, dd, H-5, $J_{4,5}$ 3.0 Hz, $J_{5,6}$ 8.5 Hz), 3.90–3.93 (2H, m, H-2, H-6), 4.08 (1H, dd, H-3, $J_{2,3}$ 8.4 Hz, $J_{3,4}$ 4.1 Hz), 4.20 (1H, dd, H-4); $\delta_C$($CD_3OD$) 5.29, 64.5 (2×5, C-1, C-7), 70.9, 72.7, 74.3, 81.1, 81.5 (5×d, C-2, C-3, C-4, C-5, C-6); m/z ($NH_3$, DCI) 237 ($M+NH_{4+}$, 100%), 220 ($M+H^+$, 20%).

Example 7

α-(Aminomethyl)-1-deoxy-mannofuranose [1-Amino-2,5-anhydro-1-deoxy-D-glycero-D-talo-heptitol hydrochloride] (5). The azide (16) (0.12 g, 0.63 mmol) was stirred in methanol (5ml) at room temperature under hydrogen in the presence of 10% palladium on carbon (10 mg). After 24 h, t.l.c. (5% methanol in ethyl acetate) indicated conversion of the starting material ($R_f$ 0.3) to a single product ($R_f$ 0.0). The reaction mixture was filtered through celite, the solvent removed in vacuo, and the resulting solid purified by ion exchange chromatography with Dowex 50W-X8 using 0.5M ammonia as eluant. After freeze drying, 1-amino-2,5-anhydro-1-deoxy-D-glycero-D-talo-heptitol (5) (95 mg, 88%) was obtained as a yellowish solid. The solid was taken up in water, and the solution neutralised with dilute aqueous hydrochloric acid. Freeze drying, followed by recrystalisation from methanol/chloroform, gave 1-amino-2,5-anhydro-1-deoxy-D-glycero-D-talo-heptitol hydrochloride (5) as a colourless crystalline solid, m.p. 189° C. (dec.). (Found: C, 36.61; H, 7.27; N, 5.42. $C_7H_{16}O_5NCl$ requires C, 36.61; H, 7.02; N, 6.10%); $[\alpha]_{D20}$ +38.6° (c 1.0 in $CHCl_3$); $\delta_H$ ($D_2O$) 3.00 (1H, dd, H-1, $J_{1,1'}$ 13.4 Hz, $J_{1,2}$ 8.8 Hz), 3.18 (1H, dd, H-1′, $J_{1',2}$ 2.9 Hz), 3.52 (1H, dd, H-7, $J_{6,7}$ 5.0 Hz, $J_{7,7'}$ 12.1 Hz), 3.66 (1H, dd, H-7′, $J_{6,7'}$ 2.7 Hz), 3.80 (1H, ddd, H-6, $J_{5,6}$ 9.0 Hz), 3.87 (1H, dd, H-5, $J_{4,5}$ 2.6 Hz), 3.91 (1H, dt, H-2, $J_{2,3}$ 8.4 Hz), 4.05 (1H, dd, H-3, $J_{3,4}$ 4.1 Hz), 4.17 (1H, dd, H-4); $\delta_C$($D_2O$) 41.8, 63.1 (2×t, C-1, C-7), 69.0, 71.6, 74.3, 77.2, 79.6 (5×d, C-2, C-3, C-4, C-5, C-6); m/z (NH$_3$, DCI) 194 (M+H$^+$, 100%).

Synthesis of α-HomoDIM (4)

Example 8

2-Azido-2-deoxy-3,4:6,7-di-O-isopropylidene-D-glycero-D-talo-heptose (17). Di-isobutylaluminum hydride (1.0M in heptane, 15 ml, 15 mmol) was added, under nitrogen, to a stirred solution of the azidoactone (11) (3.99 g, 12.75 mmol) in dry THF (20 ml) at −70° C. After an additional 1 h at −70° C., the solution was allowed to stand for 6 h at −20° C. when $^1$H NMR indicated complete lactol formation. Sodium fluoride (0.5 g, 12 mmol), saturated aqueous ammonium sulphate (2 ml), and ether (40 ml) were added sequentially whereupon a white galatinous precipitate formed. The mixture was filtered and the precipitate washed with ether (2×20 ml). The filtrate and washings were combined, dried (magnesium sulphate) and the solvent removed to afford 2-azido-2-deoxy-3,4:6,7-di-O-isopropylidene-D-glycero-D-talo-heptose (17). A small amount of material was recrystallized (ether), to give a white crystalline solid, m.p. 114°–115° C. (Found: C, 49.82; H, 6.99; N, 12.99. D$_{13}$H$_{21}$O$_6$N$_3$ requires: C, 49.52; H, 6.71; N, 13.32%); $[\alpha]_{D20}$ +0.41° (C 1.0 in CHCl$_3$); $\nu_{max}$(KBr) 3400 (br, OH), 2120 (N$_3$) cm$^{-1}$; $\delta_H$(CDCl$_3$) 1.38 (6H, s, 2×Me), 1.43, 1.48 (6H, 2×s, 2×Me), 3.16 (1H, d, OH, D$_2$O exch., J$_{1,OH}$ 3.1 Hz), 3.54 (1H, dd, H-2, J$_{1,2}$ 6.8 Hz, J$_{2,3}$ 2.6 Hz), 3.62 (1H, dd, H-5, J$_{4,5}$ 1.6 Hz, J$_{4,6}$ 7.9 Hz), 4.00 (1H, dd, H-7, J$_{6,7}$ 4.3 Hz, J$_{7,7'}$ 8.7 Hz), 4.01 (1H, dd, H-7', J$_{6,7'}$ 6.0 Hz), 4.22 (1H, ddd, H-6), 4.45 (1H, dd, H-4, J$_{3,4}$ 7.8 Hz), 4.60 (1H, dd, H-3), 5.26 (1H, dd, H-1); $\delta_C$ (CDCl$_3$) 24.8, 25.6, 26.7 (3×q, 4×Me), 60.9 (d, C-2), 66.6 (t, C-7), 70.8, 72.8, 73.4, 73.6 (4×d, C-3, C-4, C-4, C-5, C-6), 92.7 (d, C-1), 109.7, 110.8 (2×s, 2×CMe$_2$); m/z (NH$_3$, DCI) 333 (M+NH$_4$+, 35%, 316 (M+H$^+$, 25%), 288 (M+H$^+$—N$_2$, 100%).

Example 9

2-Azido-2-deoxy-3,4:6,7-di-O-isopropylidene-D-glycero-D-talo-heptitol (18). The remainder of the crude lactol (17) was dissolved in methanol (20 ml) and sodium borohydride (530 mg, 14 mmol) was added over 30 min at 0° C. After an additional 1 h at 0° C. the reaction was allowed to warm to room temperature and stirred for a further 1 h. at which point t.l.c. (hexane:ethyl acetate, 1:1) indicated complete consumption of the lactol (17) (R$_f$ 0.6) to give a single product (R$_f$ 0.5). The reaction was quenched by addition of saturated aqueous ammonium sulphate (2 ml). Flash chromatography (hexane:ethyl acetate, 3:1) gave 2-azido-2-deoxy-3,4:6,7-di-O-isopropylidene-D-glycero-D-talo-heptitol (18) (3.16 g, 78% over two steps from (11)), a white crystaline solid, m.p. 74°–75° C. (ether/hexane). (Found: C, 49.14; H, 7.41; N, 13.03. C$_{13}$H$_{23}$N$_3$O$_6$ requires: C, 49.20; H, 7.31; N, 13.24%); $[\alpha]_{D20}$ −45.0° (c 1.1 in CHCl$_3$); $\nu_{max}$ (CHCl$_3$): 3550 (OH), 2110 (N$_3$) cm$^{-1}$; $\delta_H$ (CDCl$_3$) 1.37, 1.38, 1.44, 1.50 (12H, 4×s, 4×Me), 2.01 (1H, dd, HO-1, J$_{OH,1}$ 5.1 Hz, J$_{OH,1'}$ 7.0 Hz), 2.18 (1 H, d, HO-5, J$_{OH,5}$ 9.5 Hz), 3.8–4.1 (7H, m), 4.15 (1H, dd, J 6.9 Hz, J 9.6 Hz) 4.45 (1H, d, J 6.9 Hz); $\delta_C$(CDCl$_3$) 24.3, 25.1, 26.3, 26.6 (4×q, 4×Me), 61.3 (d, C-2), 63.5, 66.7 (2×t, C-1, C-7), 69.5, 74.9, 75.2, 73.3 (4×d, C-3, C-4, C-5, C-6), 108.9, 109.4 (2×s, 2×CMe$_2$); m/z (NH$_3$, DCI) 335 (M+NH$_4$+, 10%), 318 (M+H$^+$, 20%), 290 (M+H$^+$—N$_2$, 100%).

Example 10

2-Azido-1-O-tert-butyldiphenylsilyl-2-deoxy-3,4:6,7-di-O-isopropylidene-D-glycero-D-talo-heptitol (19). tert-Butyldiphenylsilylchloride (0.55 ml, 2.12 mmol) was added, under nitrogen, to a stirred solution of the diol (18) (612 mg, 1.93 mmol) and imidazole (263 mg, 3.8 mmol) in dry DMF at 0° C. The solution was then warmed to room temperature and stirred for 5 h, when t.l.c. (hexane:ethyl acetate, 3:1) showed only a trace of starting material (R$_f$ 0.3) and one major product (R$_f$ 0.7). The solvent was removed, the residue shaken with dichloromethane (30 ml) and then filtered. Evaporation and purification by flash chromatography (hexane:ethyl acetate, 4:1) gave 2-azido-1-O-tert-butyldiphenylsilyl-2-deoxy-3,4:6,7-di-O-isopropylidene-D-glycero-D-talo-heptitol (19) (983 mg, 92%), a viscous oil; $[\alpha]_{D20}$ −35.0° (c 1.05 in CHCl$_3$); $\nu_{max}$(film) 3500 (br, OH), 2125 (N$_3$) cm$^{-1}$; $\delta_H$ (CDCl$_3$) 1.09 (9H, s, Me$_3$C), 1.34, 1.38, 1.41, 1.45 (12H, 4×s, 4×Me), 2.13 (1H, d, OH, J$_{OH,5}$ 9.1 Hz, D$_2$O exch.), 3.91 (3H, m), 4.05 (4H, m), 4.23 (1H, dd, J 6.9 Hz, J 9.6 Hz), 4.44 (1H, d, J 6.9 Hz), 7.43 (6H, m), 7.73 (4H, m); $\delta_C$(CDCl$_3$) 19.0 (s, CMe$_3$), 24.3, 25.3, 26.4 (3×q, 3×Me), 26.5 (q, CMe$_3$), 26.7 (q, Me), 61.2 (d, C-2), 64.9, 66.9 (2×g, C-1, C-7), 69.6, 74.0, 75.3, 76.4 (4×d, C-3, C-4, C-5, C-6), 108.7, 109.4 (2×s, 2×CMe$_2$), 127.9, 129.9 (2×d, 2×Ar-C), 133.0 (s, Ar-C), 135.8 (d, Ar-C); m/z (NH$_3$, DCI) 528 (M+H$^+$—N$_2$, 20%), 510 (M+H$^+$—N$_2$—OH$_2$, 100%).

Example 11

2-Azido-1-O-tert-butyldiphenylsilyl-2-deoxy-3,4:6,7-di-O-isopropylidene-D-glycero-D-talo-heptitol (20). Methanesulphonyl chloride (0.20 ml, 2.0 mmol) was added, under nitrogen, to a stirred solution of the alcohol (19) (447 mg, 0.81 mmol) and 4-N,N-dimethylaminopyridine (20 mg, 0.16 mmol) in dry pyridine (5 ml) at room temperature. After 12 H, t.l.c. (hexane:ethyl acetate, 3:1) indicated complete consumption of starting material (R$_f$ 0.6) to give a single product (R$_f$ 0.5). The solvent was removed and the residue dissolved in chloroform (50 ml), washed with water (2×30 ml) and dried (magnesium sulphate). Removal of the solvent followed by flash chromatography (hexane:ethyl acetate, 6:1) gave 2-azido-1-O-tert-butyldiphenylsilyl-2-deoxy-3,4:6,7 -di-O-isopropylidene-5-O-methanesulphonyl-D-glycero-D-talo-heptitol (20) (458 mg, 90%), a white crystalline solid, m.p. 90°–91° C. (Found C, 56.70; H, 6.85; N, 6.86. C$_{30}$H$_{43}$N$_3$O$_8$SSi requires c, 56.85; H, 6.84; N, 6.63%); $[\alpha]_{D20}$ −45.3° (c 1.0 in CHCl$_3$); $\nu_{max}$(film) 2108 (N$_3$) cm$^{-1}$; $\delta_H$(CDCl$_3$) 1.09 (9H, s, Me$_3$C), 1.39, 1.44, 1.48, 1.57 (12H, 4×s, 4×Me), 3.06 (3H, s, MeSO$_3$), 3.9–4.1 (4H, m), 4.13 (1H, dd, J 6.2 Hz, J 8.8 Hz), 4.3 (2 H, m), 4.38 (1H, dd, J 1.9 Hz, J 6.2 Hz), 5.15 (1H, dd, H-5, J 1.8 Hz, J 4.9 Hz), 7.43 (6H, m), 7.71 (4H, m); $\delta_C$ (CDCl$_3$) 19.00 (s, CMe$_3$), 25.0, 25.4, 26.0, 26.2 (4×q, 4×Me), 26.5 (q, CMe$_3$), 39.8 (q, MeSO$_3$), 59.5 (d, C-2), 64.6, 75.8 (2×t, C-1, C-7), 74.0, 75.5, 76.0, 77.7 (4×d, C-3, C-4, C-5, C-6), 109.4, 110.2 (2×s, 2×CMe$_2$), 128.0, 130.2 (2×d, 2×Ar-C), 133.0 (s, Ar-C), 136.0 (d, Ar-C); m/z (NH$_3$, DCI) 651 (M+NH$_4$+, 30%), 606 (M+H$^+$—N$_2$, 100%).

Example 12

2-Azido-1-O-tert-butyldiphenylsilyl-2-deoxy-3,4-O-isopropylidene-5-O-methanesulphonyl-D-glycero-D-talo-heptitol (21). The diacetonide (20) (463 mg, 0.73 mmol) was dissolved in 1,4-dioxan (3 ml) and 80% aqueous acetic acid (6 ml) was then added. The reaction was stirred at 50° C. for 1.5 h when t.l.c. (hexane:ethyl acetate, 2:1) showed only a trace of starting material ($R_f$ 0.8), a major product ($R_f$ 0.3) and a minor product ($R_f$ 0.1). The solvent was removed at 20° C. and the residue co-evaporated with toluene (3×5 ml). Purification by flash chromatography (hexane:ethyl acetate, 1:1) gave three products; the first to be eluted was unreacted starting material (20) (14 mg, 3%); the second fraction was the diol, 2-azido-1-O-tert-butyldiphenylsilyl-2-deoxy-3,4-O-isopropylidene-5-O-methanesulphonyl-D-glycero-D-talo-heptitol (21) (344 mg, 79%), a viscous oil. (Found: C, 54.71; H, 6.94; N, 6.91. $C_{27}H_{39}N_3O_8SSi$ requires C, 54.61; H, 6.62; N, 7.08%); $[\alpha]_{D20}$ −40.5° (c 1.0 in $CHCl_3$); $\nu_{max}$ (film) 3450 (br, OH), 2110 ($N_3$) cm$^{-1}$; $\delta_H$ ($CDCl_3$) 1.09 (9H, s, $Me_3C$), 1.33, 1.35 (6H, 2×s, 2×Me), 2.7 (1H, br. s, OH), 3.13 (3H, s, $MeSO_3$), 3.65 (1H, br. s, OH), 3.8 (5H, m), 4.10 (1H, m), 4.21 (1H, dd, J 5.6 Hz, J 10.0 Hz), 4.46 (1H, t, J 5.5 Hz), 5.16 (1H, t, H-5, J 5.5 Hz), 7.43 (6H, m), 7.70 (4H, m); $\delta_C$ ($CDCl_3$) 19.0 (s, $CMe_3$), 25.4 (q, $CMe_3$), 26.7 (q, $CMe_2$), 39.3 (q, $MeSO_3$), 60.1 (d, C-2), 62.1, 64.9 (2×t, C-1, c-7), 72.9, 74.7, 76.6, 78.4 (4×d, C-3, C-4, C-5, C-6), 109.5 (s, $CMe_2$), 127.9, 130.0 (2×d, 2×Ar-C), 132.8 (s, Ar-C), 136.0 (d, Ar-C). Continued elution yielded the tetrol, 2-azido-1-O-tert-butyldiphenylsilyl-2-deoxy-5-O-methanesulphonyl-D-glycero-D-talo-heptitol (16 mg, 4%), a viscous oil which rapidly decomposed, $\delta_H$: 1.09 (9H, s, $Me_3C$), 3.13 (3H, s, $MeSO_3$), 3.5–3.9 (8H, m), 4.04 (4H, m), 4.98 (1H, d, H-5, J 6.2 Hz), 7.44 (6H, m), 7.69 (4H, m); $\delta_C$ 18.9 (s, $CMe_3$), 26.6 (q, $CMe_3$), 38.2 (q, $MeSO_3$), 62.3, 63.9 (2×t, C-1, C-7), 64.9 (d, C-2), 70.2, 70.6, 71.4, 79.2 (4×d, C-3, C-4, C-5, C-6), 128.1, 130.2 (2×d, 2×Ar-C), 132.6 (s, Ar-C), 135.7 (d, ArC).

Example 13

5,6-Anhydro-2-azido-1-O-tert-butyldiphenylsilyl-2-deoxy-3,4-O-isopropylidene-D-glycero-L-allo-heptitol (22). Saturated methanolic barium methoxide solution (0.5 ml) was added to a stirred solution of the diol (21) (457 mg, 0.77 mmol) in dry methanol (5 ml) at 0° C. After 30 min at room temperature, t.l.c. (hexane:ethyl acetate, 1:1) indicated no starting material ($R_f$ 0.25) and a single product ($R_f$ 0.5). The solution was filtered, a small amount of solid carbon dioxide added to the filtrate and the solvent removed. Flash chromatography (hexane:ethyl acetate, 4:1) gave 5,6-anhydro-2-azido-1-O-tert-butyldiphenylsilyl-2-deoxy-3,4-O-isopropylidene-D-glycero-L-allo-heptitol (22) (354 mg, 925), a colourless oil. (Found: C, 62.74; H, 7.27; N, 8.14. $C_{27}H_{39}N_3O_8SiS$ requires C, 62.75; H, 7.09; N, 8.44%); $[\alpha]_{D20}$ −12.3° (c 1.0 in $CHCl_3$); $\nu_{max}$ (film) 3450 (br, OH) cm$^{-1}$; $\delta_H$ ($CDCl_3$) 1.10 (9H, s, $Me_3C$), 1.30, 1.36 (6H, 2×s, 2×Me), 1.70 (1H, br s, OH), 3.20 (2H, m, H-5, H-6), 3.63 (1H, ddd, H-2, $J_{1,2}$ 2.8 Hz, $J_{1',2}$ 6.8 Hz, $J_{2,3}$ 9.7 Hz), 3.74 (1H, m, H-7), 3.90 (1H, dd, H-1', $J_{1,1'}$ 10.8 Hz), 4.00 (1H, br d, H-7'), 4.02 (1H, t, H-4), 4.06 (1H, dd, H-1), 4.15 (1H, dd, H-3, $J_{3,4}$ 5.7 Hz), 7.46 (6H, m), 7.73 (4H, m); $\delta_C$ ($CDCl_3$) 19.0 (s, $CMe_3$), 25.0 (q, Me), 26.5 (q, $CMe_3$), 27.5 (q, Me), 52.2, 56.5 (2×d, c-5, C-6), 61.0, 64.9 (2×t, C-1, C-7), 61.6 (d, C-2), 75.2, 77.0 (2×d, C-3, C-4), 109.5 (s, $CMe_2$), 127.9, 130.0 (2×d, 2×Ar-C), 133.0 (s, Ar-C), 135.8 (d, Ar-C); m/z ($NH_3$, DCI) 470 (M+H$^+$—$N_2$, 100%).

Example 14

5,6-Anhydro-2-azido-7-O-tert-butyldimethylsilyl-1-O-tert-butyldiphenylsilyl-2-deoxy-3,4-O-isopropylidene-D-glycero-L-allo-heptitol (23). tert-Butyldimethylsilyl chloride (122 mg, 0.81 mmol) was added, under nitrogen, to a stirred solution of the epoxyalcohol (22) (270 mg, 0.54 mmol) and imidazole (120 mg, 1.76 mmol) in dry DMF (5 ml) at 0° C. The solution was allowed to warm to room temperature. After 2 h, t.l.c. (hexane:ethyl acetate, 1:1) showed only a trace of starting material ($R_f$ 0.35) and one major product ($R_f$ 0.8). The solvent was then removed and the residue dissolved in ether (10 ml), washed with water (5 ml) and brine (2×5 ml), and dried (magnesium sulphate). Removal of the solvent and purification by flash chromatography (hexane:ethyl acetate, 6:1) gave 5,6-anhydro-2-azido-7-O-tert-butyldimethylsilyl-1-O-tert-butyldiphenylsilyl-2-deoxy-3,4-O-isopropylidene-D-glycero-L-allo-heptitol (23) (280 mg, 84%), a viscous oil. $[\alpha]_{D20}$ −3.3° (c 0.55 in $CHCl_3$); $\nu_{max}$ (film) 2110 ($N_3$) cm$^{-1}$; $\delta_H$ ($CDCl_3$) 0.09 (6H, s, $SiMe_2$), 0.91, 1.09 (18H, 2×s, 2×$Me_3C$), 1.29, 1.36 (6H, 2×s, 2×Me), 3.11 (2H, br m, H-5, H-6), 3.66 (1H, ddd, H-2, $J_{1,2}$ 2.8 Hz, $J_{1',2}$ 6.7 Hz, $J_{2,3}$ 9.6 Hz), 3.75 (1H, dd, H-7', $J_{6,7}$ 4.5 Hz, $J_{7,7}$ 12.0 Hz), 3.88 (1H, dd, H-1', $J_{1',1}$ 10.8 Hz), 3.93 (1H, dd, H-7, $J_{7,6}$ 2.8 Hz), 4.01 (1H, t, H-4, J 6.0 Hz), 4.05 (1H, dd, H-1), 4.14 (1H, dd, H-3, $J_{3,4}$ 5.7 Hz); $\delta_C$ ($CDCl_3$) −5.50 (q, $SiMe_2$), 18.5, 19.0 (2×s, 2×$CMe_3$), 25.1 (q, Me), 25.7, 26.6 (2×q, 2×$CMe_3$), 27.6 (q, Me), 52.3, 56.7 (2×d, C-5, C-6), 61.6 (d, C-2), 62.5, 65.1 (2×t, C-1, C-7), 73.5, 787.1 (2×d, C-3, C-4), 109.4 (s, $CMe_2$), 127.9, 130.0 (2×d, 2×Ar-C), 133.0 (s, Ar-C), 135.9 (d, Ar-C); m/z ($NH_3$, DCI) 584 (M+H$^+$—$N_2$, 50%).

Example 15

7-O-tert-Butyldimethylsilyl-1-O-tert-butyldiphenylsilyl-2,5-dideoxy-2,5-imino-3,4-O-isopropylidene-D-glycero-D-talo-heptitol (24). The silyl protected azidoepoxyalcohol (23) (150 mg, 0.409 mmol) and palladium black (7 mg) were stirred in ethanol (4 ml) at room temperature under hydrogen. After 24 h, t.l.c. (hexane:ethyl acetate, 2:1) indicated complete consumption of starting material ($R_f$ 0.8) to give a single product ($R_f$ 0.35), the cyclised amine. The reaction mixture was filtered through a small celite pad, washing with ethanol, and the solvent removed to give a colourless oil. Purification by flash column chromatography (hexane:ethyl acetate, 1:8) gave 7-O-tert-butyldimethylsilyl-1-O-tert-butyldiphenylsilyl-2,5-dideoxy-2,5-imino-3,4-O-isopropylidene-D-glycero-D-talo-heptitol (24) (107 mg, 75%), a colourless oil. $[\alpha]_{D20}$ −11.0° (c 1.0 in $CHCl_3$); $\nu_{max}$ (film) 3200 (br OH & NH) cm$^1$; $\delta_H$ ($CDCl_3$) 0.08 (6H, s, $SiMe_2$), 0.89, 1.07 (18H, 2×s, 2×$Me_3C$), 1.33, 1.50 (6H, 2×s, 2×Me), 2.02 (br OH, NH), 3.14 (1H, dd, H-5, $J_{4,5}$ 4.3 Hz, $J_{5,6}$ 6.1 Hz), 3.34 (1H, t, H-2, J 6.2 Hz), 3.60 (4H, br m, H-1, H-1', H-7, H-7'), 3.86 (1, br m, H-6), 4.68 (1H, d, H-3, $J_{3,4}$ 5.7 Hz), 4.75 (1H, dd, H-4), 7.39 (6H, m), 7.65 (4H, m); $\delta_C$ ($CDCl_3$) −5.6 (q, $SiMe_2$), 18.1, 19.0 (2×s, 2×$CMe_3$), 23.7, 25.7 (2×q, 2×Me), 25.9, 26.8 (2×q, 2×$CMe_3$), 62.2, 65.0 (2×d, C-2, C-5), 64.4, 65.8 (2×t, C-1, C-7), 71.6, 82.6, 83.6 (3×d, C-3, C-4, C-6), 111.2 (s, $CMe_2$), 127.9, 129.8 (2×d, 2×Ar-C), 133.2 (s, Ar-C), 135.7 (d, Ar-C); m/z ($NH_3$, DCI) 586 (M+H$^+$, 100%).

Example 16

α-HomoDIM [2,5-dideoxy-2,5-imino-D-glycero-D-talo-heptitol] (4). The cyclised amine (24) 52 mg, 0.09 mmol) was stirred in trifluoroacetic acid:water, 1:1 (2 ml) for 48 h. Removal of the solvent and purification by ion exchange chromatography with Dowex 50W-X8

(H+) then gave, after freeze drying, the free base as a gum. Addition of dilute hydrochloric acid and freeze drying gave the hydrochloride salt of 2,5-dideoxy-2,5-imino-D-glycero-D-talo-heptitol (4) (16 mg, 78%), m.p. 148°-149° C. (methanol/chloroform). (Found D, 36.30; H, 7.25; N, 5.83. $C_7H_{16}NO_5Cl$ requires C, 36.60; H, 7.02; N, 6.09%); $[\alpha]_{D20}$ +26.9° (c 1.0 in $H_2O$); $\nu_{max}$ (KBr disc) 3350 (broad OH & NH), 2950 cm$^{-1}$; $\delta_H$ ($D_2O$) 3.59 (3H, m, H-2, H-5, H-7), 3.67 (1H, dd, H-7′, $J_{7,7'}$ 12.1 Hz, $J_{7'6}$ 4.2 Hz), 3.76 (1H, dd, H-1, $J_{1,1'}$ 12.6, $J_{1,2}$ 3.8 Hz), 3.88 (1H, dd, H-1′, $J_{1'2}$ 3.3 Hz), 4.02 (1H, m H-6), 4.17 (1H, dd, H-4, $J_{3,4}$ 3.7 Hz, $J_{4,5}$ 9.3 Hz), 4.33 (1H, br t, H-3); $\delta_C$ ($D_2O$) 59.2, 62.1 (2×d, C-2, C-5), 63.3, 63.7 (2×t, C-1, C-7), 68.4, 71.5, 72.2 (3×d, C-3, C-4, C-6); m/z ($NH_3$, DCI) 194 (M+H+, 100%).

REFERENCES

[1] Winchester, B, and Fleet, G. W. J., *Glycobiology*, 1992, 2, 199; Legler, G., *Adv. Carbohydr. Chem. Biochem.*, 1990, 48, 319.

[2] Furui, H., Kiso, M., and Hasegawa, A., *Carbohydr. Res.*, 1992, 229, C1.

[3] Rhinehart, B. L., Robinson, K. M., King, C. H., and Liu, P. S., *Biochem. Pharmacol.*, 1990, 39, 1537; Liu, P. S., *J. Org. Chem.*, 1987, 52, 4717.

[4] B. Woynarowska, B., Wilkiel, H., Sharma, M., Carpenter, N., Fleet, G. W. J., and Bernacki, R. J., *Anticancer Res.*, 1992, 12, 161; Liu, P. S., Kang, M. S., and Sunkara, P. S., *Tetrahedron Lett.*, 1991, 32, 719.

[5] Jones, I. M., and Jacob, G. S., *Nature*, 1991, 330, 74; Taylor, D. L., Sunkara, P. S., Liu, P. S., Kang, M. S., Bowlin, T. L. and Tyms, A. S., *AIDS*, 1991, 5, 693; Stephens, E. G., Monck, E., Reppas, K., and Butfiloski, E. J., *J. Virol.*, 1991, 65, 1114.

[6] Lees, W. J. and Whiteside, G. M., *Bioorg. Chem.*, 1992, 20, 173; Hassan, M. E., *Gazz. Chim. Ital.*, 1992, 122, 7; Fairbanks, A. J., Carpenter, N. M., Fleet, G. W. J., Ramsden, N. G., Cenci de Bello, I., Winchester, B. G., Al-Daher, S. S., and Nagahashi, G., *Tetrahedron*, 1992, 48, 3365.

[7] Burgess, K., and Henderson, I., *Tetrahedron*, 1992, 48, 4045; St.-Denis, Y., and Chan, T. H., *J. Org. Chem.*, 1992, 57, 3078; Herczegh, P., Kovacs, I., Szilagyi, L., Zsely, M., and Sztaricskai, F., *Tetrahedron Lett.*, 1992, 33, 3133; Gradnig, G., Berger, A., Grassberger, V., Stuetz, A. E., and Legler, G., *Tetrahedron Lett.*, 1991, 32, 4889.

[8] Bischoff, J., and Kornfeld, R., *Biochem. Biophys, Res. Commun.*, 1984, 125, 324; Fuhrmann, U., Bause, E., Legler, G., and Ploegh, H., *Nature*, 1984, 307, 755.

[9] de Gasperi, R., Daniel, P. F., and Warren, C. D., *J. Biol. Chem.*, 1992, 267, 9706.

[10] White, S. L., Nagai, T., Akiyama, S. K. Reeves, E. J. Grzegorzewski, K., and Olden, K., *Cancer. Commun.*, 1991, 3, 83; Olden, K., Breton, P., Grzegorzewski, K., Yasuda, Y., Gause, B. L., Oredipe, O. A., Newton, S. A., and White, S. L., *Pharmacol. Ther.*, 1991, 50, 285.

[11] Fleet, G. W. J., Ramsden, N. G., and Witty, D. R., *Tetrahedron*, 1989, 45, 319.

[12] Carpenter, N. M., Fleet, G. W. J., and Cenci di Bello, I., winchester, B., Fellows, L. E., and Nash, R. J., *Tetrahedron Lett.*, 1989, 30, 7261.

[13] Beacham, A. R., Bruce, I., Choi, S., Doherty, O., Fairbanks, A. J., Fleet, G. W. J., Skead, B. M., Peach, J. M., Saunders, J., and Watkin, D. J., *Tetrahedron: Asymm.*, 1991, 2, 883.

[13] Choi, S., Bruce, I., Fairbanks, A. J., Fleet, G. W. J., Jones, A. H., Nash, R. J., and Fellows, L. E., *Tetrahedron Lett.*, 1991, 32, 5517.

[15] Mantell, S. J., Fleet, G. W. J., and Brown, D., *Tetrahedron Lett.*, 1992, 33, 4503.

[16] Fleet, G. W. J., Bruce, I., Firdnar, A., Harladsson, M., Peach, J. M., and Watkins, D. J., *Tetrahedron*, 1990, 46, 19.

[17] Denci di Bello, I., Fleet, G., Namgoong, S.-K., Tadano, K.-I., and Winchester, B., *Biochem. J.*, 1989, 259, 855.

[18] Winchester, B. G., Cenci di Bello, I., Richardson, A. C., Nash, R. J., Fellows, L. E., Ramsden, N. G., and Fleet, G., *Biochem. J.*, 1990, 269, 227.

[19] Dumas, D. P., Kajimoto, T., Liu, K. K.-C., Wong, W.-H, Berkowitz, D. B., and Danishefsky, S. J., *Bioorg. Med. Chem. Lett.*, 1992, 2, 33.

Various other examples will be apparent to the person skilled in the art after reading the present disclosure without departing from the spirit and scope of the invention. It is intended that all such other examples be included within the scope of the appended claims.

What is claimed is:

1. 2,5-Dideoxy-2,5-imino-D-glycero-D-talo-heptotol.

2. A method for the synthesis of 1,5-dideoxy-2,5-imino-D-glycero-D-Talo-heptitol (4) comprising carrying out the reactions in solution phase and in about stoicheometric proportions of reactants shown by formulas in the following reaction steps:

a. reducing 2-azido-2-deoxy-3,4:5,6-di-O-isopropylidene-D-glycero-D-talo-heptono-1,5lactone (11) with di-isobutylaluminum hydride to give the corresponding lactol (17),

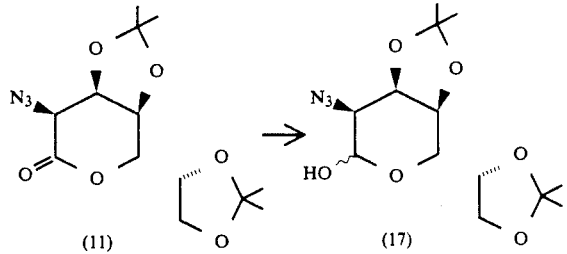

b. reacting the lactol (17) with alkali metal borohydride to provide ring opening and give the diol (18),

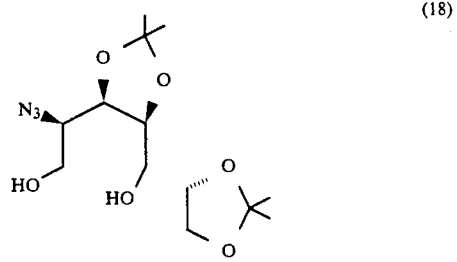

c. reacting the diol (18) with tert-butyldiphenyl-silylchloride to protect the primary hydroxyl group as the tert-butyldiphenylsilyl ether (19),

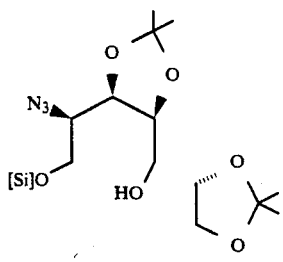
(19)

d. esterifying the hydroxyl of the tert-butyldiphenyl-silyl ether (19) at C-5 with mesyl chloride to give azidomesylate (20),

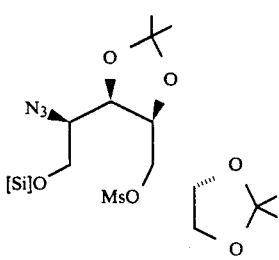
(20)

e. selectively hydrolyzing the terminal acetonide at C-6, C-7 in the azidomesylate (20) with organic acid to give monoacetonide (21),

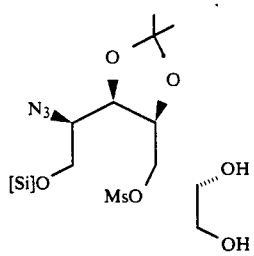
(21)

f. reacting the monoacetonide (21) with barium methoxide to give epoxide (22),

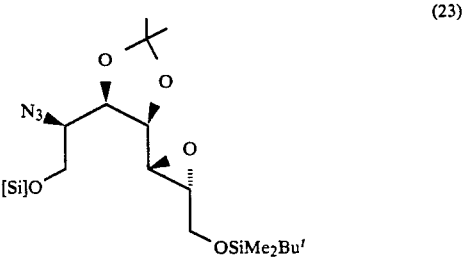
(22)

g. reacting the epoxide (22) with tert-butyldimethylsilylchloride to protect the primary hydroxyl group as the tert-butyldimethylsilyl ether (23),

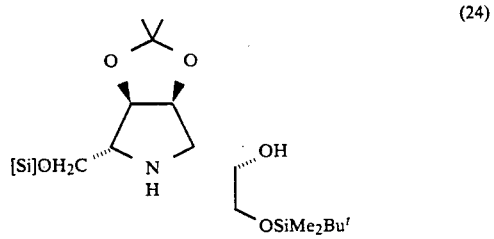
(23)

h. hydrogenating the tert-butyldimethylsilyl ether (23) in the presence of palladium black to give the protected pyrrolidine (24), and

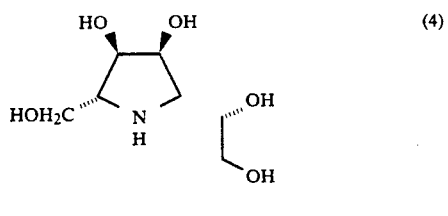
(24)

i. removing all the hydroxyl protecting groups in the protected pyrrolidine (24) by acid hydrolysis to give the desired 2,5-dideoxy-2,5-imino-D-glycero-D-talo-heptitol (4)

(4)

* * * * *